United States Patent [19]

Timmis et al.

[11] Patent Number: 5,119,588
[45] Date of Patent: Jun. 9, 1992

[54] METHOD AND APPARATUS FOR CULTURING AUTOTROPHIC PLANTS FROM HETEROTROPHIC PLANT MATERIAL

[75] Inventors: Roger Timmis, Olympia; Mary E. Kreitinger, Fall City; Michael J. Yancey, Puyallup, all of Wash.

[73] Assignee: Weyerhaeuser Company, Tacoma, Wash.

[21] Appl. No.: 589,052

[22] Filed: Sep. 27, 1990

Related U.S. Application Data

[63] Continuation-in-part of Ser. No. 416,826, Oct. 3, 1989, abandoned.

[51] Int. Cl.⁵ .............................................. A01G 9/02
[52] U.S. Cl. ............................................. 47/58; 47/73; 47/84; 47/85; 435/240.4; 435/240.45; 435/299; 435/300
[58] Field of Search ............. 47/58, 69, 73, 77, 84–87; 435/240.4, 299, 311, 313, 297, 298, 300, 301

[56] References Cited

U.S. PATENT DOCUMENTS

| | | | |
|---|---|---|---|
| 3,022,605 | 2/1962 | Reynolds | 47/84 |
| 3,384,993 | 5/1968 | Kane | 47/58 |
| 3,739,522 | 6/1973 | Greenbaum | 47/87 |
| 3,784,783 | 7/1973 | Sokolies | 47/69 |
| 4,118,890 | 10/1978 | Shore | 47/84 |
| 4,299,920 | 11/1981 | Peters | 435/299 |
| 4,324,859 | 4/1982 | Saxholm | 435/299 X |
| 4,463,522 | 8/1984 | Lindemann | 47/58 |
| 4,586,288 | 5/1986 | Walton | 47/87 X |
| 4,615,883 | 10/1986 | Nelsen et al. | 424/84 |
| 4,769,945 | 9/1988 | Motoyama et al. | 47/58 X |
| 4,829,006 | 5/1989 | Smith et al. | 435/301 |
| 4,908,315 | 3/1990 | Kertz | 435/240.4 |
| 4,957,866 | 9/1990 | Gupta et al. | 435/240.4 |
| 5,035,866 | 7/1991 | Wannlund | 435/301 X |

FOREIGN PATENT DOCUMENTS 2085702  5/1982  United Kingdom .................. 47/87

OTHER PUBLICATIONS

Verhagen and Wann; *Plant Cell, Tissue and Organ Culture* 16:103–111 (1989).
Hakman and von Arnold, *J. Plant Physiol.* 121:149–158 (1985).
Mathur et al., *Plant Science* 60:111–116 (1989).
STAR*PAC ™ promotional literature entitled "Leap Into The Future."

(List continued on next page.)

*Primary Examiner*—James R. Feyrer
*Attorney, Agent, or Firm*—Klarquist, Sparkman, Campbell, Leigh & Whinston

[57] ABSTRACT

A method and apparatus is disclosed for growing embryonic or other undeveloped plant material in a controlled, biologically sterile environment to produce plants capable of surviving in soil in an uncontrolled environment. Cloned somatic embryos of a particular plant are individually embeddeed in separate sterile plugs comprised of a soil-like particulate medium. A volume of aqueous medium comprising a source of carbon and energy for the somatic embryos, and plant growth regulating substances, if required, is added to each plug. The sterile plugs are then isolated from the ambient environment while permitting exposure to light and atmospheric gases sufficient to effect development of photosynthesis in the developing embryos in the plugs. While in such isolation, the resulting plantlets develop roots and shoots. The resulting autotrophic plants are then removed from isolation and the growth medium is altered to remove the carbon and energy source to limit the capacity of the medium to support plant harming microbes. The plants are then transplanted. Several embodiments are disclosed involving compartmentalized trays and covering films or bags by which embryo-containing plugs are kept isolated from each other and from the environment during development of the embryos.

38 Claims, 5 Drawing Sheets

OTHER PUBLICATIONS

Ulian and Smith draft paper entitled "Enhanced in Vitro Tuberization of Solanum."

Tinus et al., "How to Grow Tree Seedlings in Containers in Greenhouses," USDA Forest Service General technical Report RM-60, p. 81 (May 1979).

Gupta and Durzan, "Biotechnology of Somatic Polyembryogenesis and Plantlet Regeneration in Loblolly Pine," *Bio/Technology* 5:147-151 (1987).

Durzan and Gupta, "Somatic Embryogenesis and Polyembryogenesis in Douglas-Fir Cell Suspension Cultures," *Plant Science* 52:229-235 (1987).

Boulay et al., "Development of Somatic Embryos from Cell Suspension Cultures of Norway Spruce (*Picea abies* Karst.)," *Plant Cell Rep.* 7:134-137 (1988).

Gupta and Durzan, "Plantlet Regeneration via Somatic Embryogenesis from Subcultured Callus of Mature Embryos of *Picea abies (Norway Spruce)*," *In Vitro Cell. & Dev. Biol.* 22:685-688 (1986).

Gupta and Durzan, "Somatic Polyembryogenesis from Callus of Mature Sugar Pine Embryos," *Bio/Technology* 4:643-645 (1986).

Bhansali et al., "Mass Cloning of Date Plantlets Through Repetitive Somatic Embryogenesis," *J. Plant Anat. Morphol.* (Jodhpur) 5:73-79 (1988) (abstract).

Taloumis, "Gardening with Plastics," *Horticulture* (Sep. 1953), pp. 369, 376, 380.

Evans et al., "*Handbook of Plant Cell Culture*," vol. 4, pp. 486-487 (1986).

Parrott et al., "Optimization of Somatic Embryogenesis and Embryo Germination in Soybean," *In Vitro Cell. & Dev. Biol.* 24:817-820 (1988).

Anadarajah et al., "Enhanced Vigor of Dry Somatic Embryos of *Medicago sativa* L. with Increased Sucrose," *Plant Science* 71:261-266 (1990).

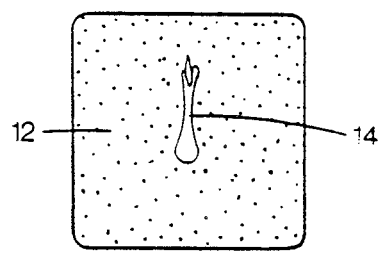
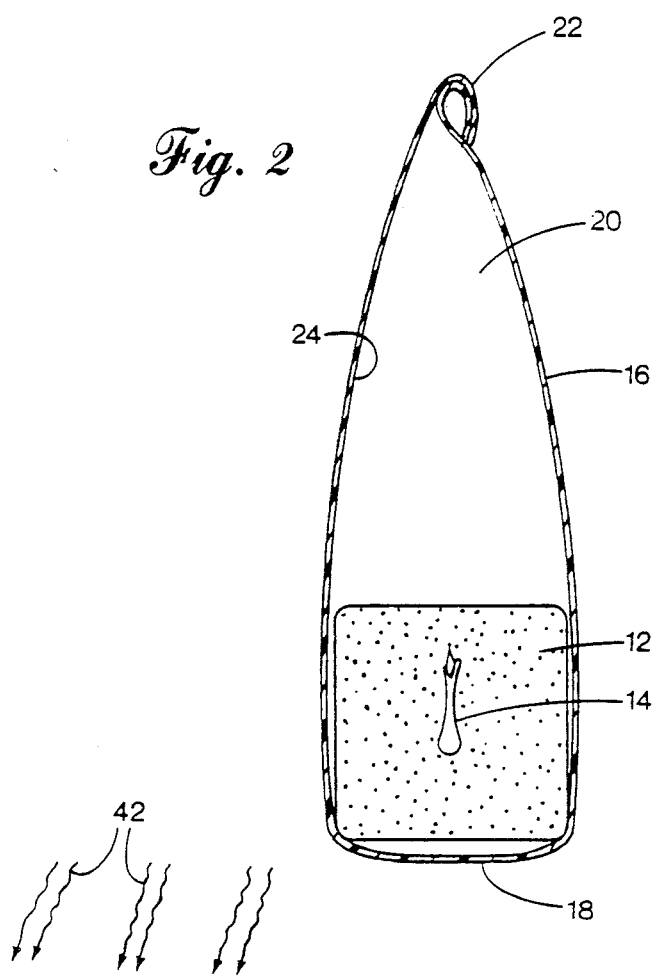
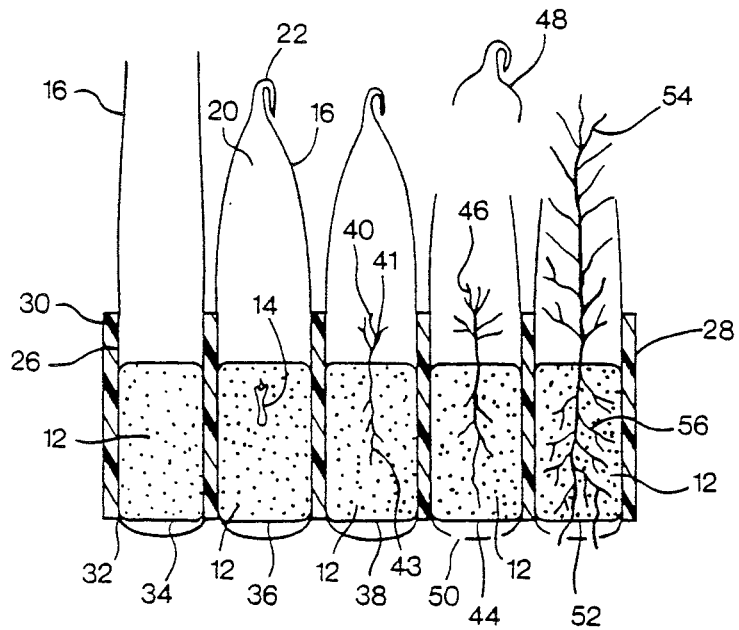

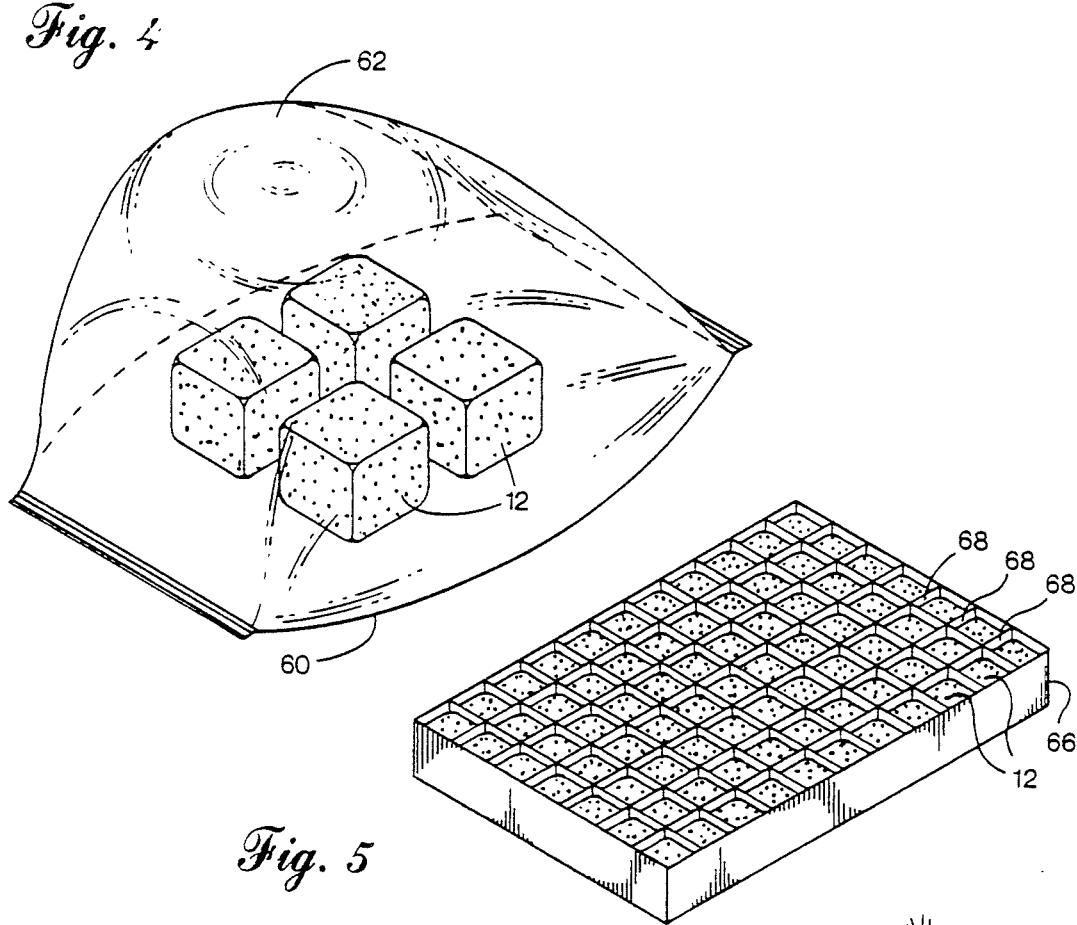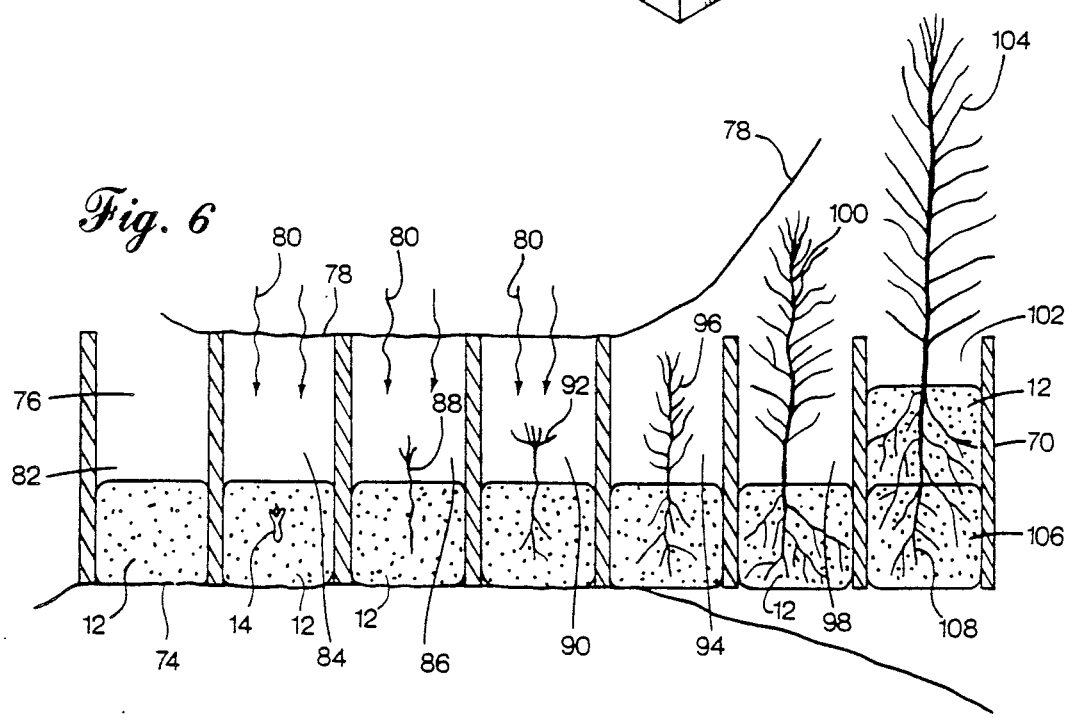

METHOD AND APPARATUS FOR CULTURING AUTOTROPHIC PLANTS FROM HETEROTROPHIC PLANT MATERIAL

CROSS REFERENCE TO RELATED APPLICATION

This application is a continuation-in-part of co-pending U.S. application Ser. No. 07/416,826, filed on Oct. 3, 1989, now abandoned.

FIELD OF THE INVENTION

This invention relates to the growing of plants. In particular, the present invention pertains to the growing of embryonic or other undeveloped plant material in a controlled, biologically sterile environment to produce plants capable of surviving in soil in an uncontrolled environment.

BACKGROUND OF THE INVENTION

Recent advances in plant cell and tissue culture have made possible the asexual production of multiple, genetically identical copies of a source plant, termed plant cloning. Such culture is typically begun with a unit of plant tissue containing totipotent plant cells obtained from a source plant. Totipotent cells have both the complete genetic information to develop into separate complete plants without involving the sexual union of gametes and the ready capacity to develop into complete plants if cultured in vitro under favorable conditions. Totipotent plant cells are obtainable from such areas of a plant as meristematic tissue and plant embryonic tissue. Meristematic cells are undifferentiated plant cells from which differentiated cells arise. Meristematic cells divide to yield other meristematic cells as well as differentiated cells that elongate and further specialize to form structural tissues and organs of the plant. Meristematic cells are located, for example, at the extreme tips of growing shoots or roots, in buds, and in the cambium layer of woody plants. Plant embryonic tissue can be found inside a seed of the source plant as a zygotic embryo (developed from a zygote, which is a cell resulting from the union of gametes during fertilization).

Plant production by tissue culture techniques has several advantages over production involving the sexual process of pollination and seed production. First, tissue culture is fast; plantlets can be obtained in much less time than required for flower production, pollination, consequent seed production and maturation, and germination. Second, tissue culture can be prolific; extremely large numbers of plantlets can be simultaneously produced. Third, plants produced by tissue culture are all genetically identical with predictable characteristics, except for an occasional spontaneous mutant. In contrast, each progeny plant resulting from sexual reproduction is the result of a genetic recombination process and so is genetically different from all other progeny plants. As a result, the characteristics of the progeny from sexual reproduction are not as predictable.

Because of the advantages of plant production by tissue culture, the process is being increasingly employed in such industries as ornamental plant production and agriculture. A current method of choice, because of its low cost, begins with the procurement of an explant or excised piece of totipotent plant tissue removed from a desirable source plant. The explant is placed on a culture medium (usually in the form of a gel) containing plant growth nutrients and plant growth hormones. Eventually, the explant evolves a macroscopically formless mass of tissue, frequently called callus tissue, (comprising undifferentiated or partially differentiated totipotent plant cells) which is transferred to an embryo-development medium containing hormones that stimulate the formation of somatic embryos. Somatic embryos appear similar to the zygotic embryos found in seeds, but, in contrast with zygotic embryos, are genetically identical to the source plant. As can be surmised, the above process of forming and culturing somatic embryos on gels or liquids requires aseptic techniques from start to finish.

Somatic embryos are too undeveloped to survive in a natural soil environment. Somatic embryos cannot yet produce their own carbon compounds or derive energy from photosynthesis and they lack their own energy source, such as an endosperm tissue. Therefore, somatic embryos are cultured with an energy source, such as sucrose. This culture medium is highly susceptible to invasion by microorganisms, which can result in death or retard the growth of the embryos Hence, the development of somatic embryos into viable plantlets capable of surviving outside aseptic culture conditions has heretofore proved to be a very difficult and inefficient process.

The ever increasing need for large numbers of genetically identical trees of optimal genotype in the various timber industries has prompted researchers to investigate tissue culture methods for production of tree embryos and plantlets. A classic paper by Hakman and von Arnold, *J. Plant Physiol.* 121:149–158 (1985) discloses the production of embryonic callus tissue from explanted zygotic embryos of Norway Spruce, *Picea abies*. Aseptic culture conditions are described which are suitable for generation of somatic embryos from the callus tissue. However, that paper notes poor success in producing viable plantlets from the somatic embryos.

Verhagen and Wann, *Plant Cell, Tissue, and Organ Culture* 16:103–111 (1989) discloses the initiation of embryonic callus formation and generation of somatic embryos from explanted Norway Spruce zygotic embryos. These researchers did not attempt to develop optimal conditions for producing plantlets from the somatic embryos.

Durzan and Gupta, *Plant Science* 52:229–235 (1987) discloses some success in producing somatic embryos of Douglas-fir, *Pseudotsuga menziesii*, but poor success in converting the somatic embryos to viable plantlets.

As can be seen, while several researchers have developed techniques favorable to the production of somatic embryos of plants from explanted zygotic embryos or callus tissue, there is still a need for a practical method of converting cultured somatic embryos, or their equivalent, of plants to viable plantlets, especially plantlets that can survive outside aseptic culture conditions and grow into mature plants.

SUMMARY OF THE INVENTION

The present invention is a method and apparatus for growing cultured embryonic or other undeveloped living plant material in a controlled biologically sterile environment until the plant material becomes able to carry on photosynthesis for continued growth and development into a mature plant. At this time the plant material no longer requires a growth medium of a type which promotes the growth of microorganisms from the ambient environment. In other words at a time when the plant no longer requires a growth medium of the type which encourage the rapid growth of plant-damaging microorganisms naturally occurring in the external environment, the plant is exposed to the environment and the growth medium is altered so that it no longer encourages microorganisms growth. The invention has special utility for the large-scale rearing of cloned plant somatic embryos propagated in tissue culture to seedling-sized plants ready for mechanical or manual transplanting to a natural soil environment such as in a nursery or similar facility. The present invention has been successfully employed in the simultaneous production of a multitude of genetically identical seedlings of commercially valuable timber trees from somatic embryos at a high rate of survival.

Cloned somatic embryos of a particular plant species, or other analogous units of immature plant material requiring growth and acclimation to form healthy seedlings, are "sown" (embedded) in a presterilized plug comprised of a mass of soil-like particulate medium. The plug is moistened with an aqueous solution of a source of carbon and energy for the embryo. The aqueous solution may also include mineral nutrients as well as plant hormones (if required). The plugs containing the embryos are maintained in a sterile humid environment wherein the germinating embryos are exposed to atmospheric gases and to light at an appropriate intensity and spectral composition to facilitate the development of photosynthetic capability in the germinating embryos. In the sterile humid environment, the embryos germinate to eventually form roots and one or more shoots bearing leaves. Upon reaching a sufficient state of development, typically when the plants have developed several true leaves, meaning that the plants are seedling size, the plants are exposed to the ambient non-sterile environment, further grown in the plugs, and transplanted into soil without disturbing the original plug surrounding the roots. Watering of the plants after removal from isolation washes the aqueous medium out of the plugs, thereby altering the medium and decreasing the possibility of the aqueous medium promoting excessive fungal or other biological growth in the plug.

Another aspect of certain embodiments of the invention involves biologically isolating the plugs from one another until such time as the plants have grown sufficiently such that the external energy source can be removed to make the plant-growth medium much less conducive to growth of biological contaminants.

One exemplary technique for separating and isolating the plugs is to enclose each plug containing an embryo or other plant material and an aqueous medium in an individual container, such as a small plastic bag, sized to allow sufficient room for the germinating embryo to develop a shoot and leaves without obstruction. A plurality of such plug-containing bags or other containers can be held in a tray comprised of many normally vertical, rigid-walled cells, each cell sized to hold a single bag. These containers typically biologically isolate the individual cells so that, in the event one cell is contaminated with microorganisms, one cell does not contaminate the other cells. When the germinating embryos reach a suitably developed state, the tops and bottoms of the individual containers are opened to promote further growth and development of the plants, for example, to seedling size. In the case of plastic bags, the bags can be opened by simply cutting off their tops and puncturing the bottoms.

Another exemplary technique for isolating a number of plugs from the environment, each containing an embedded plant embryo or other plant material and aqueous medium, is to enclose the multiple plugs in a single large container, such as a plastic bag, either with or without the use of a tray comprised of cells to support each plug. However, although advantageous in promoting plant growth, the individual plugs or cells, unless biologically isolated from each other, can be contaminated from other cells.

Another isolation technique is to support each plug in a cell of a tray possessing a multiple of such cells, where the bottom of each cell of the tray is sealed from the ambient environment and from the other cells, such as with a plastic film adhered to the bottom of the tray and peripherally around the bottom rim of each cell using a contact adhesive. In such a manner, the bottom of each cell of the tray is isolated from the ambient environment and is biologically isolated from the bottoms of all other cells of the tray. In addition, the cell-defining walls of the tray biologically isolate the plugs. Preferably, the cells are relatively deep to allow sufficient space for unobstructed growth of the plant embryos. Also, the tops of the cells are similarly isolated, such as by a plastic film attached in a similar manner. As a result, all the cells of the tray are biologically isolated both from the ambient environment and from all other cells on the tray. The top plastic films are preferably fabricated of a transparent or translucent flexible material allowing controlled passage of atmospheric gases into each cell, such as oxygen and carbon dioxide, as well as ambient light sufficient for proper growth and development of the germinating embryos. Other top coverings should have similar light and gas passage characteristics. When the resulting plants reach a state of development wherein they have adequate root and shoot development as well as photosynthetic capability, the top and bottom covers are opened or removed, as by peeling off, melting, dissolving, or puncturing the covers in the case of films, thereby exposing each cell and its contents to the ambient environment. The plants then undergo further development and growth, such as to seedling size, before transplantation.

Another technique for isolating a number of plugs containing embryos in individual cells on a tray is to cover the plug-containing tray with a second inverted tray. The second tray may be adhered to the plug-containing tray, such as by a contact adhesive applied around the top rim of each cell. The "bottoms" of both trays are covered, such as with a plastic film as described above. When the embryos reach a sufficient state of growth and development where they can be removed from isolation, the covers are removed. For example, both the film on the bottom of the plug-containing tray and the entire second tray may be simply peeled off the plug-containing tray to expose each cell to the ambient environment.

Another technique for isolating plug-containing cells is to overlay the plug in each cell of a tray with a layer of particulate, hydrophobic material which prevents growth of microorganisms from spores settling on the top of the hydrophobic layer through to the underlying plug while permitting passage therethrough of atmospheric gases and water vapor. The germinating embryo or other plant material rapidly penetrates through the hydrophobic layer to the ambient atmosphere for continued growth and development while preserving the sterility of the plug material. The bottom of such a tray is typically isolated from the environment and the plugs are isolated from one another, as by a plastic film adhered to the tray as described above that can be peeled away when the plants reach a sufficiently developed state.

A primary object of the present invention is to provide a method of and apparatus for converting cultured somatic embryos, or other plant material capable of growing into plants, into viable plants at a high survival rate, the viable plants being sized to be able to survive outside aseptic culture conditions and grow into mature plants.

Another object is to provide such a method and apparatus to effect a conversion of cloned plant somatic embryos on a large scale that is convenient and economically feasible to perform.

Another object is to provide such a method and apparatus to effect such conversion of such plant somatic embryos and other plant material in a single explant-handling step from aseptic culture vessel to soil-like medium in a container ready for eventual transplantation.

Another object is to provide such a method and apparatus whereby cultured plant somatic embryos or other plant material are germinated in soil-like medium so as to develop roots capable of surviving and functioning in a soil-like environment simultaneous with developing their first shoots and leaves, thereby obviating an acclimation step upon being ultimately transplanted as seedling-size plants to natural soil.

Another object is to provide such a method and apparatus whereby the plants, when they reach seedling or other suitable size, can be transplanted in to natural soil without disturbing the roots in the soil-like medium in which the roots originally germinated.

Another object is to provide such a method and apparatus whereby the carbon and energy requirements of the plant somatic embryos or other plant material are supplied by simple carbohydrate compounds until the resulting plants are capable of satisfying such requirements by their own photosynthesis.

Another object is to provide such a method and apparatus whereby both isolating the plant somatic embryos and other plant material from the ambient environment during growth and development thereof and subsequent release from isolation are simple and easy to perform, even on a large scale and in an automated process.

The invention includes the above objects and features taken alone and in combination. These and other features, objects and advantages of the present invention will become more apparent with reference to the following description and the drawings.

BRIEF DESCRIPTION OF THE DRAWINGS

FIG. 1 is a front sectional view of a sterile plug of soil-like particulate medium according to the present invention showing a plant somatic embryo embedded therein.

FIG. 2 is a vertical sectional view of the sterile plug of FIG. 1 enclosed in a small plastic bag for isolation from the ambient environment, according to one embodiment of the present invention.

FIG. 3 is a front sectional view of a tray comprised of multiple cells, each sized to accommodate one of the plug-containing bags of FIG. 2, each successive cell in FIG. 3 showing the contents thereof at a progressively later moment in time during the growth and development of a plant somatic embryo.

FIG. 4 is an isometric view of multiple sterile plugs of FIG. 1 enclosed together in a plastic bag for isolation from the ambient environment, according to another embodiment of the present invention.

FIG. 5 is an isometric view of a tray comprising multiple cells for containing individual plugs.

FIG. 6 is a vertical sectional view of the tray of FIG. 5 with a means for isolating the plugs from the ambient environment and from one another, each successive cell in this figure showing the contents thereof at a progressively later moment in time.

DETAILED DESCRIPTION OF THE PREFERRED EMBODIMENTS

Figure 7:
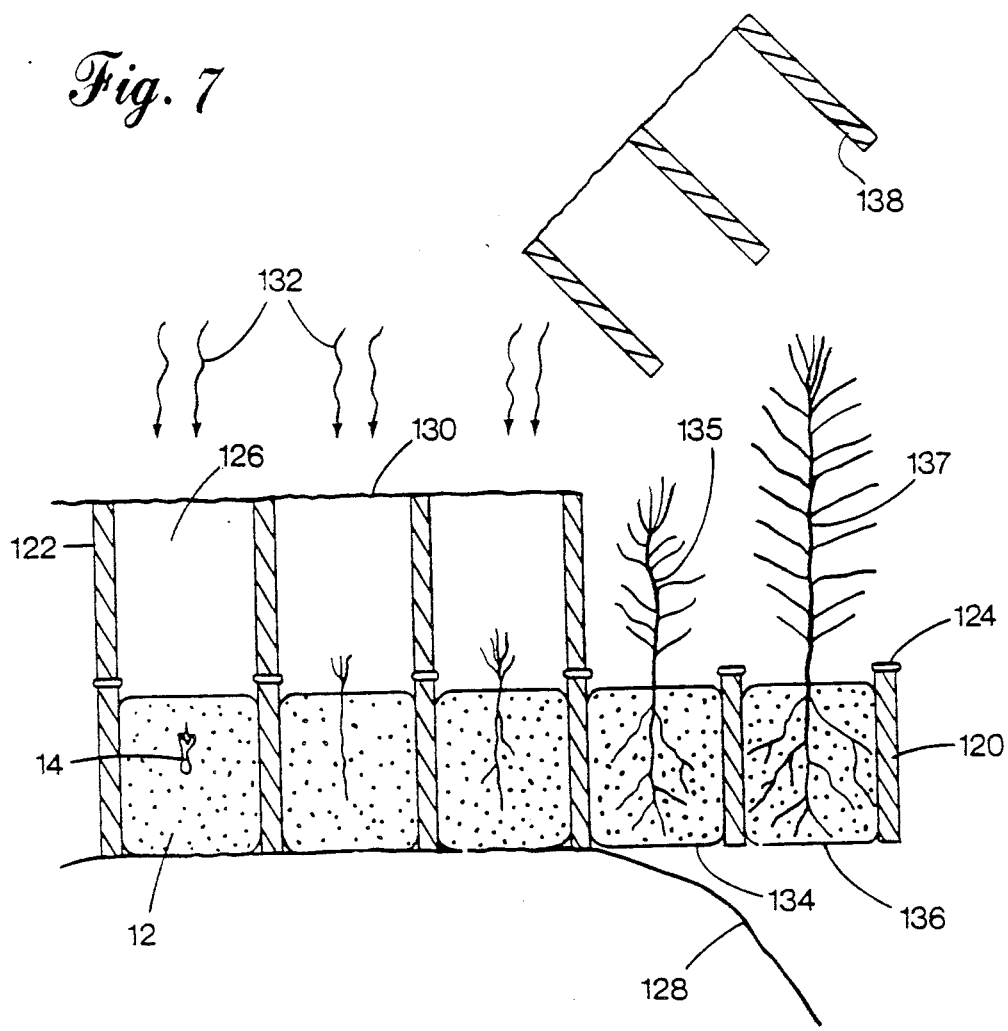
FIG. 7 is a vertical sectional view of a plug-containing tray which is similar to FIG. 6 except that the tray is formed of top and bottom sections.

The following definitions will assist in the understanding of this detailed description.

As used herein, "heterotrophic" plant material is plant tissue, including cultured somatic embryos of plants, that is unlikely to survive outside of aseptic, rigorously controlled culture conditions, such as found in a laboratory. Because such material is either incapable or at most weakly capable of photosynthesis, heterotrophic plant material requires an extraneous source of carbon and energy in the growth medium, such as sucrose, to maintain normal growth and development at a desired rate. As a result, heterotrophic plant material survives poorly or not at all in normal soil.

"Autotrophic" plant material is able to supply its carbon and energy requirements through photosynthesis. As a result, no external energy-supplying compounds are required in order for the plant material to sustain a normal growth rate. Therefore, cultural milieu is not apt to be swamped by microorganisms. Hence, autotrophic plant material is able to survive and grow under normal soil conditions.

A "callus" is, at least at a macroscopic level, a mass of unorganized and undifferentiated totipotent plant cells which, at least at a macroscopic level, are either unconnected or loosely connected, generally arising from culturing of an explant.

An "explant" is a piece of plant tissue excised from a donor plant for culturing in vitro as the source of cultured plant tissues.

A "plantlet" is a small plant more immature than a seedling. A plantlet is usually heterotrophic, but may also be autotrophic.

A "somatic embryo" is a plant embryonic structure arising from an explanted zygotic embryo or other totipotent plant tissue.

A "zygotic embryo" is a plant embryo that developed directly from the zygote produced from the sexual fusion of gametes. For example, the embryo found in a seed is a zygotic embryo.

A "bud" is an organized mass of various plant tissues from which a particular plant organ or organs will develop.

A "meristem" is a group of undifferentiated plant cells which divide to form more meristematic cells as well as somewhat differentiated cells capable of elongation and further development into plant organs and structures.

A "seedling" as used herein includes, in addition to a plant developed from a germinating seed, an autotrophic plantlet grown from a somatic embryo according to the present invention that is sufficiently developed for transplantation into soil.

Referring to FIG. 1, a plug 12 comprising a volume of particulate medium is shown in which is embedded a unit of heterotrophic plant material 14. Although the plug 12 is shown with a square cross section, it may have any convenient shape and cross section.

The plug 12 is comprised of a volume of any suitable particulate medium having soil-like properties for the growth of a seedling-sized or other-sized autotrophic plant that will ultimately develop from the embedded unit of heterotrophic plant material 14. Candidate particulate media include, but are not limited to, vermiculite, perlite, sand, pumice, clay particles, plastic particles, peat, as well as other suitable materials or mixtures thereof with ground bark and sawdust. Particulate media can also include various mixtures of these materials with added binders such as gels and fibers, where a sufficient proportion of the particulate material is present so as to maintain interparticle air spaces necessary for growth of roots adapted for growth in soil. Preferably, a substantial portion of the media is particulate and most preferably a major portion (e.g., about 50% or more) of the media is particulate.

It is important that the plug be comprised of a particulate medium rather than a predominantly liquid or gel-like medium. Research has shown that plants grown in a gel or liquid tend to have weak roots that lack root hairs. When such plants are transplanted to soil, the existing roots usually die and new roots must be generated by the plant, which consumes limited energy resources in the plant, delays maturation, and lowers the plant's survival rate. Particulate and soil-like media possess intergranular pore spaces for air and water, which stimulate development of stronger roots possessing the root hairs essential for absorbing moisture, gases, and nutrients from soils. Waterlogged soils and gels simply contain too much water and insufficient air for proper root development. A "waterlogged" soil is one substantially without interstitial air because of a substantial filling of all of the intergranular soil spaces with water.

The embedded unit of heterotrophic plant material 14 is generally a somatic embryo as shown in FIG. 1. However, the heterotrophic plant material may also be any viable unit of living plant material containing totipotent cells capable of growing under controlled conditions in particulate medium into a complete autotrophic plant possessing normal roots and shoots. One source of such heterotrophic plant material is liquid culture of plant somatic embryos derived from explanted zygotic embryos of the source plant. This process, such as described by Durzan and Gupta, *Plant Science* 52:229–235 (1987), involves several culture steps involving different gel and liquid media containing mineral nutrients, organic compounds to supply carbon and energy, specific plant hormones, and water. Other sources of suitable heterotrophic plant material are cultured meristematic tissue, explanted zygotic embryos, cultured bud tissues, totipotent callus tissues, and the like, produced by any of a number of currently practiced plant micropropagation techniques generally involving use of gel media. For convenience, and not to be construed as a limitation, the unit of heterotrophic plant material embedded in the plug will be referred to in the remaining portions of this specification generally as a somatic embryo.

The plug 12 should be sterile before embedding the somatic embryo 14. Any suitable sterilization method may be used, including autoclaving, chemical treatment (e.g., sodium hypochlorite solution), irradiation, and exposure to a sterilizing gas, such as ethylene oxide. High-temperature sterilization methods, such as autoclaving, may be unsatisfactory for certain materials such as peat because the heat causes a release of toxic compounds such as phenolics and ammonia.

Somatic embryos are preferably, but not necessarily, embedded below the top surface of the plug. For example, somatic embryos of conifers such as Douglas-fir (*Pseudotsuga menziesii*), Norway Spruce (*Picea abies*) and Loblolly Pine (*Pinus taeda*) having length of 2–3 mm are typically embedded 0–10 mm below the plug surface. Larger embryos may be embedded deeper. It is preferable that the embryos be embedded vertically with the rudimentary shoot pointing upward and rudimentary root or radicle pointing downward.

The plug 12 should include other substances, in addition to the particulate medium, to support growth and development of the somatic embryo 14. The plug 12 should also contain sufficient water throughout, without being "waterlogged." In one specific example, the volumetric ratio of vermiculite to water in the plug did not exceed 11 parts vermiculite to 6.5 parts water. However, this ratio varies with the type of media, but in general requires that the interstitial voids between the particles not be substantially filled with water. In addition to not "waterlogging" the particulate medium, the total amount of liquid in the plug 12 should also not be so great as to prevent gas exchange between the somatic embryo and the atmosphere above the plug.

The water content of the plug 12 is usually satisfied by addition to the volume of dry particulate medium comprising the plug of an aqueous solution containing the appropriate profile of mineral nutrients, plant hormones (if required), and one or more compounds for supplying the carbon and energy needs of the heterotrophic somatic embryo. One example of such an aqueous medium is given in Table 1. The Table 1 medium is particularly suitable for efficient growth of heterotrophic plantlets of such conifers as Douglas-fir (*Pseudotsuga menziesii*), Norway Spruce (*Picea abies*), and Loblolly Pine (*Pinus taeda*).

TABLE 1

| Compound | Concentration | (mg/L) |
|---|---|---|
| $NH_4NO_3$ | 206.25 | |
| $KNO_3$ | 1170.00 | |
| $H_3BO_3$ | 3.1 | |
| $KH_2PO_4$ | 85.0 | |
| KI | 0.42 | |
| $Na_2MoO_4.H_2O$ | 0.125 | |
| $CoCl_2.6H_2O$ | 0.0125 | |
| $CaCl_2.2H_2O$ | 220.0 | |

TABLE 1-continued

| Compound | Concentration | (mg/L) |
|---|---|---|
| $MgSO_4.7H_2O$ | 185.0 | |
| $MnSO_4.H_2O$ | 8.45 | |
| $ZnSO_4.7H_2O$ | 4.3 | |
| $CuSO_4.5H_2O$ | 0.0125 | |
| $Na_2EDTA$ | 18.625 | |
| $FeSO_4.7H_2O$ | 13.925 | |
| myo-inositol | 100.0 | |
| thiamine | 1.0 | |
| pyridoxine | 0.5 | |
| nicotinic acid | 0.5 | |
| glycine | 2.0 | |
| sucrose | 20 | g/l |
| charcoal | 2.5 | g/l |
| pH = 5.7 | | |

It should be kept in mind, however, that addition of medium such as in Table 1 is beneficial but not necessarily required for all types of plant embryos. In general, a medium containing mineral nutrients is more efficient in most cases in promoting the growth of the heterotrophic plants, but is not necessary in all cases. In addition, the nutrients and carbon and energy source may be mixed in dry powder or particulate form into the media. Thereafter, water can be added to form the aqueous medium. The term aqueous solution or medium thus encompasses a solution formed by adding water to plugs containing these particulate nutrients and other materials as well as a solution formed by mixing these materials with water and applying the mixture to growth media. When powdered nutrients and energy sources are used, the plugs may be stored and subsequently activated by adding water when used to support the growth of plant material.

As stated above, the aqueous medium may also include one or more plant growth hormones (not listed in Table 1) to stimulate growth and development of plant structures, such as shoots or roots, from the embryo. While somatic embryos usually have a sufficiently developed rudimentary shoot and root so as to not require growth hormones in the medium, other types of heterotrophic plant material may not, such as micropropagated adventitious meristematic tissue, buds, or microcuttings. Hence, depending upon the particular type and state of development of the heterotrophic plant material embedded in the plug, plant hormones such as auxins and cytokinins may be advantageous.

The aqueous medium should be added to the plug 12 before embedding the somatic embryo 14 in the plug or immediately afterward to prevent drying of the embryo. If the dry plug is sterilized before adding the aqueous medium, the medium should also be made sterile before adding to the plug. Such sterilization can be effected by any of several current methods, including microporous membrane filtration. It is also possible to sterilize (e.g., autoclave) the plug after adding the aqueous solution to the dry particulate medium, so long as the sterilization process does not cause detrimental change to any of the solutes in the aqueous solution.

It is, of course, also important that the somatic embryo 14 be free of biological contamination before embedding it in the sterile plug 12. This is because the nutritive medium surrounding somatic embryos is easily infected by microorganisms whose rampant growth can harm the embryo. The corresponding autotrophic plant generally does not experience such problems because the growth medium used for autotrophic plants need not be embedded with sucrose or other energy sources that promote rampant microbial growth of microorganisms.

Once the somatic embryo 14 has been embedded in the sterile plug 12 containing appropriate amounts of water, mineral nutrients, if used, a source of carbon and energy, and plant growth hormones (if required), it is then necessary to isolate the plug 12 from biological contamination from, and loss of water to, the ambient environment until the somatic embryo reaches an autotrophic state. During such isolation, however, it is also necessary to allow passage to the plug of light at a favorable intensity, spectral composition, and photoperiod to stimulate the development of photosynthetic capability in the embryo. It is also necessary to supply the embryo with gases, such as carbon dioxide and oxygen, necessary for respiration, photosynthesis, and to meet other requirements of plant growth and development.

The following examples illustrate several representative ways in which one or more sterile plugs, each containing a somatic embryo and appropriate nutrient additives, can be biologically isolated from the ambient environment while still supplying light and gases needed for growth. Gas is preferably supplied via the exchange of atmospheric gases although a separate gas supply can be used. Also, light is typically supplied through a transparent cover to the plugs. The examples also present several ways in which a plurality of plugs may be simultaneously handled and isolated from the ambient environment while still keeping each plug separated from neighboring plugs. Such separation is important when working with a large number of plugs. If a non-separated plug in a large group by chance becomes biologically contaminated, the invading microorganisms can rapidly spread to other plugs in the group, possibly resulting in loss of all the somatic embryos in the group. However, if the plugs are sufficiently separated to prevent liquid contact between plugs, then accidental contamination can more easily be confined to the one or few plugs initially affected, enabling the remainder to be saved.

EXAMPLE 1

Referring to FIG. 2, one way to effect isolation of a plug 12 from biological contamination is to place the plug 12 into a container such as a small plastic bag 16 where the plug 12 rests on the bottom 18 of the bag. The bag 16 should have sufficient empty head space 20 above the plug 12 to allow room for a plantlet developing from the embryo 14 to grow out of the plug 12 and not be obstructed by the bag 16. Typically, the plug 12 has a height no greater than one-half the height of the bag 16. Although in the experiments described below the bags were specifically made for use in the laboratory, commercially available bags may be used. Star-Pac ™ bags made by AgriStar, Inc., Sealy, Tex. 77474, are a suitable example.

Since the plug 12 containing the somatic embryo 14 and aqueous medium is sterile, at least the interior surface 24 of the bag 16 should also be sterile before placing the plug 12 in the bag. It is possible, however, to place a non-sterile volume of particulate medium in the bag to form a plug and sterilize the bag and contents afterward. Then, while keeping the bag and contents sterile, a sterile volume of aqueous medium can be added to the plug and a sterile somatic embryo 14 is embedded in the plug 12 before closing and sealing the bag 16. Regardless of which method is chosen, the somatic embryo 14 must not be in the plug 12 during sterilization of the plug if the sterilization process is one that would either kill or adversely affect the embryo.

After placing the plug 12 containing the somatic embryo 14 and aqueous medium in the bag 16, the top 22 of the bag 16 is sealed such as by closing tightly, heat sealing, or otherwise. The sealed bag 16 creates a humid atmosphere in the space 20 which prevents drying of the plug 12 and embryo 14. The sealed bag also prevents incursion of microorganisms from the ambient environment to the plug.

The bag 16 not only serves to isolate the plug 12 from biological contamination, but is also preferably of a material which allows passage of light and gases necessary for plant growth and development from the ambient environment to the interior 20 of the bag 16. Hence, the bag 16 may be fabricated of a transparent or translucent material that will allow passage of light of sufficient intensity and color balance to permit photosynthesis by a plant growing inside the bag. The bag material may also be of the type of material which allows carbon dioxide and oxygen gas to pass from the ambient environment into the space 20 to satisfy the respirational and photosynthetic needs of the plant inside the bag 16. Finally, the bag 16 preferably also passes water vapor at a slow rate from the interior 20 of the bag to the ambient environment for humidity control inside the bag without an unacceptable rate of drying of the plug 12.

Candidate bag materials include high-density polyethylene, polypropylene, and fluorinated ethylenepropylene. Each of these materials, in a thickness of about 1 mil, has an oxygen permeability of less than 1300 cc/(100 in$^2$·24 hours·atmosphere) (i.e., 1300 GTR units, wherein GTR refers to gas transmission rate) in a "normal" ambient atmosphere, a permeability to water vapor of 6 g/(100 in$^2$·24 hr) (i.e., 6 VTR units, wherein VTR refers to vapor transmission rate) in a "normal" ambient atmosphere, and a light transmissivity permitting photosynthesis.

Oxygen permeability can be nearly zero where the space 20 is large and the bag 16 is opened relatively early to remove the contents from isolation (e.g., when a coniferous plantlet reaches the cotyledon stage). In such a case, impermeable materials such as glass and thick rigid films are suitable. An oxygen permeability value closer to the stated limit would be required where the volume 20 is small, the bag surface area is small, or if the plant inside needed to develop to a more advanced autotrophic state before removal from isolation (e.g., elongated epicotyl stage for coniferous plants; dry weight about 10 mg or more per plant). Usually, however, oxygen permeability is within the range of from 200 to 600 GTR units, which is satisfactory for most purposes. The oxygen permeability can be significantly lower, even for a small space containing a large plant, if the concentration of oxygen in the ambient atmosphere is correspondingly increased.

Carbon dioxide permeability of bag materials satisfying the above criteria for oxygen permeability, water vapor permeability, and light transmissivity is usually somewhat greater than the oxygen permeability. This carbon dioxide permeability is preferred, especially for the development of plants to a more advanced state before removal from isolation. Because of this fortuitous relationship of carbon dioxide permeability to oxygen permeability, a bag material satisfying the oxygen-permeability criterion is normally satisfactory with respect to carbon dioxide permeability.

A relatively slow rate of water vapor transmission prevents an excess rate of drying of the plug 12 when the bag 16 is in a normal ambient atmosphere. However, the rate can be decreased if the relative humidity of the ambient atmosphere is high.

The above-noted bag materials are particularly preferred because they can be autoclaved, thereby allowing bags to first be filled with non-sterile plugs and aqueous medium, then sterilized before adding the somatic embryo 14, which may streamline the overall procedure. If another method of sterilization is used, such as gas or radiation, many other transparent or at least translucent plastic films or containers of other materials of a suitable permeability can be used, such as polyvinyl chloride.

In one experiment, open-ended cylindrical bags approximately 20 mm diameter by 95 mm long were formed from transparent polypropylene sheets (0.038 mm or 1.5 mil thick) and from high-density polyethylene (0.026 mm or 1 mil thick) by heat-sealing the edges together. Each bag had an internal volume of about 30 mL. Each bag was filled with 7 to 10 mL of fine dry vermiculite, autoclaved at 121° C. for 30 minutes, and allowed to cool in a sterile environment. Five mL of sterile aqueous medium according to Table 1 were added to the vermiculite plug in each bag. A somatic embryo of Norway Spruce (*Picea abies*) was embedded 0 to 10 mm beneath the top surface of each plug. Each bag was then either heat-sealed to close or folded over and paper-clipped at the top, placed in a supporting grid structure to keep the bags oriented vertically, then placed in a controlled-environment chamber under favorable conditions of light and temperature. After 34 days, 60 of 64 somatic embryos had germinated and emerged 10 to 15 mm above the plug surface. There appeared to be no significant difference in germination success with heat-sealed bags compared to bags that had been folded over and paper-clipped. After an additional 36 days, the epicotyls (embryonic plant stems above the cotyledons) had elongated 5 to 15 mm above the cotyledons of each surviving plant. The "seedlings" by that time had reached a stage where they could continue growth autotrophically after the tops of the bags had been removed.

In FIG. 3, plural bags 16, each containing a plug 12, are shown being maintained in an upright position by placing each bag 16 in a separate cell 26 on a tray 28 comprised of a multiplicity of cells. The array of cells in the tray 28 may be constructed by interlocking a series of panels 30 to form multiple cells having square or rectangular transverse dimensions (see FIG. 5). Alternatively, the cells may be cylindrical or have any other suitable geometric shape. Rigid-walled cells having vertical sides are preferred for ease of removal of plugs at time of transplantation of the plants in the cells. These trays may be of plastic, metal or any other material, although the trays are typically rigid to provide support to the bags. An example of a suitable tray for this purpose is the MINIPLUG tray from the Weyerhaeuser Company, Tacoma, Washington, possessing 256 cells per tray, each cell having about a $\frac{3}{4} \times \frac{3}{4}$ inch square transverse section and a depth of about 1$\frac{1}{4}$ inch, which is particularly suitable for conifer embryos.

The cells 26 of the tray 28 may have closed or open bottoms (FIG. 3 showing open bottoms which are more suitable for certain types of transplanting machines such as the machine used with the MINIPLUG tray). It is important with open-bottomed trays that each bag be retainable in its respective cell when the tray is lifted off a horizontal surface. A friction-fit of the bags in the cells is sufficient for retaining the bags 16 in cells 26 such as the MINIPLUG type.

In the tray shown in FIG. 3, the bags 16 may be loaded into the cells either before or after filling and sealing the bags. Such loading of bags into cells and placing of a plug containing aqueous medium and a somatic embryo into each bag is a process readily performable manually or using automated equipment.

FIG. 3 also illustrates, in a left-to-right series of cells, a chronological sequence in which a somatic embryo embedded in a plug sealed in a bag grows and develops in the interior environment of the bag to an autotrophic plant with shoot and roots capable of continued growth and development after removal from the aseptic environment in the bag. The first cell 34 contains a bag 16 in which a plug 12 has been placed, indicating that an open bag 16 containing a plug 12 can be loaded into each cell of a tray and sterilized before a somatic embryo is embedded in each plug. Alternatively, the loading of each bag with a plug, an embryo, and the aqueous medium, followed by sealing of the bag, can be performed before the bag is inserted into an empty cell.

The second cell 36 in FIG. 3 contains a bag 16 with a sealed top 22 containing a sterile plug 12 in which a somatic embryo 14 has been embedded. The plug 12 also contains a volume of an aqueous medium such as that of Table 1. The head space 20 above the plug 12 contains a sterile, humid atmosphere undergoing a slow rate of exchange of oxygen gas, carbon dioxide gas, and water vapor through the bag with the ambient environment.

The third cell 38 contains a bag 16 with a sealed top 22 containing a developing plantlet 40 as it would appear several days after that shown in the second cell 36. In cell 38, the original somatic embryo has grown to form a plantlet 40 with a shoot portion 41 protruding out of the plug 12 and a root portion 43 extending downward through the particulate medium of the plug 12. Incident light, indicated by the arrows 42, passes through the bag 16 from the ambient environment to supply the plantlet 40 with sufficient light, particularly red and blue wavelengths of the visible spectrum, to stimulate development of photosynthetic capability in the plantlet 40.

In the fourth cell 44, the plantlet 46 has developed to a sufficiently autotrophic state such that it can be removed from biological isolation. One way to break the isolation is to cut off the top 48 of the bag and puncture or cut the bottom 50 of the bag. Since the plug 12 is now exposed to air, regular watering prevents the plug 12 from drying out. Watering also washes any residual carbon- and energy-supplying compounds from the plug 12. Although the plantlet 46 is exposed to various soil bacteria and fungi after being released from isolation, the removal of these compounds decreases the possibility of rampant microbial growth of microorganisms in the plug 12 that can harm the plant.

If the bag 16 is fabricated of a biodegradable plastic film, it is possible for each bag 16 to decompose away, essentially leaving only the plug 12 and plantlet 46 in the cell 44 by the time the plantlet 46 has reached a size where it is ready for transplantation. In this case, the step of opening the top and bottom of the bag is eliminated.

The fifth cell 52 of FIG. 3 shows a plantlet 54 of transplantable seedling size. As can be seen, the roots 56 of the plantlet 54 are beginning to protrude from the plug 12.

One benefit of using trays with multiple cells is that a large number of somatic embryos may be simultaneously raised from a heterotrophic state to autotrophic seedling size without having to perform any operations on the embryos after embedding them in their respective plugs until time to transplant the resulting seedlings. In fact, it is possible to automate the entire process of placing plugs in bags, sterilizing plugs and bags, embedding embryos in plugs, adding aqueous media, sealing the bags, placing loaded bags in cells, exposing the sealed bags to light, recovering the resulting plantlets from isolation after they have reached an autotrophic state, watering the plantlets, and transplanting the resulting seedlings in a nursery or other site for continued growth.

FIG. 4 shows another way in which sterile plugs 12 containing embedded somatic embryos and aqueous medium can be isolated from biological contamination. A single, large plastic bag 60 is employed to contain a number of such plugs 12, but the plugs 12 are not packed into cells. Instead, the multiple plugs 12 in the bag 60 are merely placed in a single-layer bag to isolate them from the environment. The cells may be abutting, but are preferably physically separated or spaced from each other to inhibit cross-contamination. The single, large bag 60 must have sufficient head space 62 above the plugs 12 to allow room for the embryos in the plugs to grow until they can be released from isolation. The disadvantage of placing multiple plugs 12 in a single isolation environment is that if one or more cells become inadvertently contaminated with foreign biological growth, it is easier for the contamination to spread to other plugs, even if the plugs are spaced apart as in FIG. 4, compared to individually isolated plugs as in FIG. 3.

The single bag 60 of FIG. 4 can also be utilized to biologically isolate an entire tray 66 such as the tray shown in FIG. 5 comprised of multiple sterile cells 68, each cell 68 containing a sterile plug 12 comprised of an embedded somatic embryo and volume of aqueous medium. Such a tray 66 can have either an open or closed bottom, depending in part upon how well the plug 12 can remain packed in its respective cell 68 whenever the tray 66 is lifted off a horizontal surface. Bottomless cells are preferred if the tray 66 will be used in transplanting machinery where each plug 12 containing an autotrophic seedling is pushed downward out of its cell into a hole formed in the soil at the transplanting site.

EXAMPLE 2

In this example, illustrated in FIG. 6, a tray 70 comprised of multiple, typically rigid-walled, cells is used to contain a plurality of plugs 12. The depth or height of each illustrated cell is such to allow sufficient space above the plug for growth of plantlets before they are released from isolation. Preferably, although not necessary in all embodiments, the depth or height is at least twice the height of the plugs contained therein to provide the desired spacing. Also, and again not necessarily for all embodiments, assuming the cell walls bound a plug, the height is preferably at least twice the largest transverse dimension of a single cell. Each illustrated cell is vertically oriented with an open bottom defined by a bottom rim of the cell and an open top defined by a top rim of the cell. The collective bottom rims of the cells of the tray define a bottom planar surface of the tray and the collective top rims of the cells define a top planar surface of the tray. Also, the cell walls may be of plastic or another material which blocks the passage of biological contaminants so that the risk of passage of contaminants from one cell to an adjacent cell and through the cell wall is eliminated.

Before placing a sterile plug 12 in its respective cell, a sterile plastic film 74 or other cover is adhered to the planar bottom surface of the tray, such as by using a contact adhesive. The film may be adhered peripherally around the bottom rim of each cell. In that way, the bottom of each cell is isolated from the bottoms of all other cells of the tray to minimize the risk of cross-contamination of the cells. A sterile plug 12 is placed in the lower portion of each cell, and in contact with the bottom cover. Again, a head space 76 exists in the cell above the plug 12 to allow unobstructed emergence of the growing plantlets from the plugs and development of shoots and leaves.

A somatic embryo 14 is embedded in each plug 12 along with a volume of aqueous medium such as in Table 1. After loading all the cells of the tray with sterile plugs containing embryos, a cover, such as plastic film 78, is secured to the top surface of the tray 70. The cover may be secured in the same manner as the film 74 across the bottom of the tray. In this manner, each cell is isolated both from the ambient environment and from all neighboring cells. The plastic films 78, 74 covering the tops and bottoms of the cells, respectively, obviate the need for a bag enclosing the entire tray 70.

As with the plastic bags described above in Example 1, the plastic film 78 adhering to the top of the tray has sufficient permeability to oxygen and carbon dioxide gases as well as water vapor to allow for proper development of the plantlets without excessive drying of the plugs 12. The film 78 may also be transparent or translucent, allowing passage, through the film, of light at a sufficient intensity and spectral composition to stimulate photosynthesis. The criteria for bags in Example 1 with respect to light transmissivity are generally applicable to the film 78. Although not required, it is advantageous that the bottom film have similar gas permeability characteristics as the top film. Also, as explained above, the trays, plugs and media may be sterilized after these elements are assembled.

During incubation of the somatic embryos in the cells, the plugs 12 of the tray 70 are exposed to light impinging on the cells, indicated by arrows 80. The light is typically directed vertically downward to minimize shadows on the developing embryos from the cell walls. Such light exposure ensures that the growing embryos develop sufficient photosynthetic capability so as to become autotrophic. A tray constructed of a transparent material minimizes shadowing of the light and may improve light penetration to the surface of the plug, especially if the cells are particularly deep.

When the plantlets become sufficiently developed in size and have reached an autotrophic state, they are released from isolation by merely peeling the plastic films 74, 78 from the tray 70. If the films 74, 78 are adhered to the tray 70 using a contact adhesive, peeling the films from the tray is simple to perform. Because of this simplicity, film peeling is readily adaptable to automation. Other top and bottom covers and cover-removal techniques may also be used (for example, covers with mechanical snap connections may be used), but it is preferable that the covers biologically isolate the adjoining cells. Also, covers can be heat sealed or fastened in any other suitable manner to the trays.

In one experiment, three trays, such as shown in FIG. 4, were each loaded with forty-two spaced apart sterile plugs containing somatic embryos of Norway Spruce (Picea abies) and sterile aqueous medium according to Table 1. The trays were each surrounded with a polypropylene bag to isolate the cells from the environment. After 54 days' incubation in a greenhouse under normal daylight, germination of the embryos was 93 percent in the first tray, 90 percent in the second tray, and 98 percent in the third tray. Within a sixty-day period, emergence of the epicotyl portion of the plantlets was 63 percent, 74 percent, and 67 percent, respectively. Virtually all of the germinated embryos eventually emerged.

FIG. 6 also illustrates, in a left-to-right series of cells, a chronological sequence similar to that shown in FIG. 3. The first cell 82 has its bottom opening covered with the film 74 as described above. A plug 12 has been placed in the cell 82 so as to rest on the surface of the plastic film 74. The tops of the cells containing the media, plug and somatic embryo 14 are covered, as by securing a plastic film 78, as shown in the second cell 84 of FIG. 6. After all the cells have been isolated from the ambient environment in this manner, the tray 70 is exposed to light, as indicated by the arrows 80. The third cell 86 of FIG. 6 shows the plantlet 88 with a shoot emerged from the surface of the plug and a small amount of root penetration into the plug 12. The plantlet 88 of the third cell 86 is still in a heterotrophic state, requiring continued isolation. The fourth cell 90 shows a heterotrophic plantlet 92 similar to the plantlet 88 of the third cell 86, but with more shoot and root development. The fifth cell 94 contains a plantlet 96 having sufficient growth and development so as to be autotrophic and therefore releasable from isolation. To release the plantlet 96 from isolation, the top and bottom covers are opened. In the case of film covers, the films 74 and 78 are merely peeled from the bottom and top, respectively, of the cell 94. The sixth and seventh cells 98, 102 show autotrophic seedlings of significantly greater growth and development than the seedling 96 shown in the fifth cell 94. In the sixth cell 98, the roots of the seedling 100 have not yet penetrated completely through the plug 12. The shoot portion of the seedling 100 is now about twice the height of the shoot portion of the plantlet 96 in the fifth cell 94. Watering of the cells following the removal of the covers washes out residual aqueous medium to thereby control rampant growth of fungus and other microbes in the cells. In the seventh cell 102, a second plug 106 has been inserted into the cell from the bottom in order to provide additional room for continued growth of the roots 108 of the seedling 104. The seedling 104 is of sufficient size to be transplanted into soil, such as at a nursery.

In a specific embodiment, zygotic embryos of Douglas-fir sown as shown in FIG. 6 were exposed to a greenhouse environment by peeling off an adhesive-coated transparent teflon film on the 28th day after sowing. Thirty-five cells were thereby exposed in each of three replicate trays. At the time of exposure, germination of the embryos was 91%, 60%, and 69% for the three replicate trays, of which 54%, 18%, and 49%, respectively, had developed true leaves. In a "control" experiment, similar zygotic embryos were germinated in agar medium (i.e., conventional technology). Eighty percent of the embryos germinated, of which 74% had developed true leaves in the same time period (28 days).

EXAMPLE 3

In this example, illustrated in FIG. 7, a tray 120, comprised of multiple-walled cells is used to contain a plurality of plugs 12 in a manner similar to that described in Example 2. Isolation of each cell from all other cells of the tray 120 and from the ambient environment can be achieved by the cell walls and top and bottom covers. These covers can be provided by adhering a plastic film to the bottom of the tray as described in Example 2 and by placing over and adhering to the plug-containing tray a second identical tray 122 in an inverted or upside-down orientation. Following this inversion, the lower or bottom surface of the second tray 122 is secured to the top surface of the plug-containing tray 120, such as by a contact adhesive 124. The use of contact adhesive facilitates the removal of the top of the second tray 122 from tray 120 when the plantlets achieve an autotrophic state. To isolate the cells, adhesive can be applied around the periphery of the top rim of each cell of tray 120 for adhering to the abutting rims of the cells of the tray 122.

In contrast to the tray of FIG. 6, the plug-containing tray 120 of FIG. 7 is only slightly deeper than the height of the plugs 12 placed therein. This is because the second tray 122 creates sufficient head space 126 above the plugs 12 for unobstructed growth of the plantlets while still in biological isolation.

As in Example 2, the bottom surface of the plug-containing tray 120 is covered, as by a plastic film 128 adhered thereto using a contact adhesive such that the film 128 is adhered circumferentially to the bottom rim of each cell. The top of the second tray 122 is likewise covered, as by a plastic film 130.

As in Example 2 the sterile plastic film 128 can be adhered to the bottom surface of a sterile plug-containing tray 120 before placing sterile plugs 12 in the tray 120. A somatic embryo 14 is embedded in each plug 12 along with a volume of sterile aqueous medium such as in Table 1. After loading all the cells, the second sterile tray 122 is inverted and adhered to the plug-containing tray 120, thereby isolating each cell both from the ambient environment and from all neighboring cells. Again, the trays, plugs and media may be sterilized after they have been assembled.

The illustrated films 128, 130 preferably have sufficient permeability to oxygen and carbon dioxide gases as well as water vapor to allow for proper development of the plantlets without excessive drying of the plugs 12. Criteria are such as described above in Example 1.

Additionally, the films 128, 130 are preferably transparent or translucent with sufficient permeability to light to encourage development of photosynthesis in the plantlets. Transmissivity criteria may be such as discussed in Example 1 for bags. The trays 120, 122 may also be constructed of a transparent material.

During incubation of the somatic embryos, the plugs 12 are exposed to light impinging as indicated by arrows 132. Such light exposure ensures that the growing embryos develop sufficient photosynthetic capabilities so as to become autotrophic.

When the plantlets become sufficiently developed in size and have reached an autotrophic state, they are released from isolation by removing the covers. In this specific embodiment, this is accomplished by merely peeling the plastic film 128 from the bottom of the plug-containing tray 120 and the second tray 122 from the top of the plug-containing tray 120 (a "peeled" second tray being depicted as tray 138 in FIG. 7). If the second tray 122 is left in place, the tops of the cells may be opened by removing film 130.

As in FIG. 6, FIG. 7 also illustrates in a left-to-right series of cells a chronological sequence in which a somatic embryo embedded in a plug grows and develops. In the fourth and fifth cells 134 and 136, respectively, the plantlets 135, 137 have matured from a heterotrophic state to an autotrophic state having well-developed roots and shoots. The plantlets 135, 137 in these last two cells are shown released from isolation.

EXAMPLE 4

Figure 8:
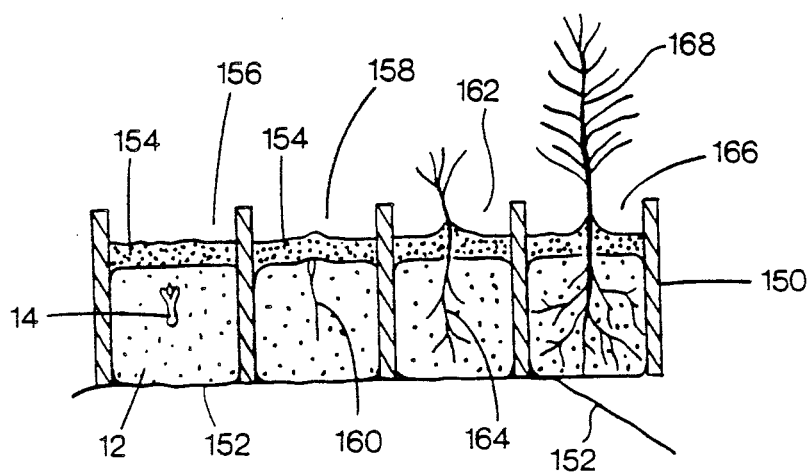
FIG. 8 is a vertical sectional view of a tray comprised of multiple plug-containing cells isolated from the ambient environment by a plug-contacting covering material, each successive cell showing the contents thereof at a progressively later moment in time.

In this example, illustrated in FIG. 8, a tray 150 is used to contain a plurality of sterile plugs 12, similar to Examples 2 and 3. Before placing a sterile plug 12 in its respective cell, a sterile plastic film 152 or other cover is secured to the planar bottom surface of the sterile tray 150, such as by adhering the film with a contact adhesive as in Examples 2 and 3. This film prevents any contaminant introduced during loading of the cells with plugs and embedding somatic embryos in the plugs from spreading from the bottom of a plug in the contaminated cell through liquid or air to adjacent cells.

After each cell is loaded with a plug 12 and each plug 12 has received a somatic embryo 14 and a volume of sterile aqueous liquid medium, the top surface of each plug 12 is covered with a sterile, non-wettable (hydrophobic) layer 154, which is preferably of a particulate material. The layer 154 biologically isolates the tops of the plugs from one another and the environment by preventing the germination or growth of any airborne microorganisms spores downward into the plug 12. However, the layer 154 does not prevent emergence of the germinating embryo 14 from beneath the layer 154. For conifer plantlets, a layer 1-3 mm thick is sufficient. The non-wettable particulate material consists, for example, of small hydrophobic plastic beads or flakes. Fine glass beads may also be used if they are siliconized or coated with a hydrophobic, anti-microbial compound such as Sylgard TM manufactured by Dow Corning. Likewise, relatively hydrophilic plastic beads may also be coated with Sylgard TM and used for this purpose.

If desired, the entire tray 150 can be further protected from biological contamination using a transparent plastic bag to enclose the entire tray. However, with layer 154, satisfactory survival of heterotrophic plantlets to an autotrophic state can be achieved without enclosing the tray in a bag or other containment in a sterile atmosphere. Nevertheless, there may be a sufficiently increased loss of water from the plug that additional precautions or modifications are required. Such modifications may include: (1) maintenance of a high relative humidity in the facility where the plantlets are grown, such as a greenhouse; (2) a supplemental vapor-impermeable piece of film lying beneath or atop the particulate covering that would be non-adhering to the tray or hydrophobic particles and pushed aside by the germinating embryo; or (3) a means of replacing lost water aseptically, e.g., by subirrigation of the plug bases through a microporous filter.

When the plantlets have reached an autotrophic state, the plastic film 152 on the bottom of the tray 150 is peeled off or otherwise removed or opened, such as described above.

FIG. 8 also illustrates in a left-to-right series of cells a chronological sequence showing the development of a somatic embryo to an autotrophic seedling. In the first cell 156, a plug 12 is shown in which a somatic embryo 14 has been embedded. This plug is covered with a layer 154 of hydrophobic, particulate material and the bottom of the cell is covered with a film 152 as described above. The second cell 158 depicts the germinating embryo 160 which has not yet penetrated the layer 154 of hydrophobic, particulate material. The third cell 162 shows a plantlet 164 that has penetrated the layer 154 of hydrophobic particulate material. The fourth cell 166 shows an autotrophic seedling 168 nearing transplantation size and at a state of development in which the bottom film 152 can be peeled off the tray 150.

To evaluate the feasibility of using particulate surface coverings for preventing contamination of the plugs while not impeding germination, and to evaluate the efficacy of various types of particulate coverings, the following experiment was performed:

Eighteen 36-cell trays were used, where the bottom surface of each tray was covered with a plastic film as disclosed in Examples 2 and 3. Each tray was sterilized before use. All cells in each tray were filled with a plug of sterile vermiculite to which was added 3.5 mL sterile liquid medium. Surface-sterile Douglas-fir zygotic embryos were sown in half the cells of each tray. Surface-sterile Norway Spruce zygotic embryos were sown in the remaining cells of each tray. After sowing, the top surface of each tray was covered with one of the following materials, where the number preceding the description of each material corresponds to the number used in the X-axis of the graph shown in FIG. 9:

"1" = "Control" using the prior-art technology of placing the embryos in sterile agar medium in separate sealed petri dishes.

"2" = "Control" using a tray having no top covering and no deliberately introduced biological contamination.

"3" = "Control" using a tray having no top covering and with deliberately introduced biological contamination.

"4" = Top of tray covered with 1-2 mm of SYL-GARD ® (Dow Corning) antimicrobial.

"5" = Top of tray covered with 3-4 mm siliconized glass beads treated with SYLGARD.

"6" = As in 5 but using glass beads without the SYL-GARD treatment.

"7" = Top of tray covered with 3-4 mm SYLGARD-treated powdered polyethylene.

"8" = Top of tray covered with powdered polyethylene only.

"9" = Top of tray covered with SYLGARD-treated candle wax flakes.

"10" = Top of tray covered with candle wax flakes only.

Treatments "5" through "10" represent the covering of cells to isolate them from biological contamination and loss of water using various examples of hydrophobic particulate material. Two trays each containing eighteen Douglas-fir embryos and eighteen Norway Spruce embryos were used for each of treatments "2" through "10" listed above. Treatment "1" was performed using sealed petri dishes each containing an embryo on sterile agar rather than trays. After sowing each tray with embryos and covering the tray as required, each tray was then individually enclosed in a sterile polypropylene bag. The bag permitted contaminating microorganisms to be deliberately introduced to a particular cell on a tray without contaminating other trays. The bag also provided a controlled environment in which to measure the rate of spread of contaminating biological growth.

With trays intended to receive biological contamination, one mL of ordinary forest soil was added to the vermiculite medium of two cells of each such tray, where each such cell was located at an opposing corner of the tray. In one "control" treatment (treatment "2"), no biological contamination was introduced. Also, in treatment "1" involving sealed petri dishes, no biological contamination was introduced. Treatments "3" through "10" received deliberately introduced contamination.

Figure 9:
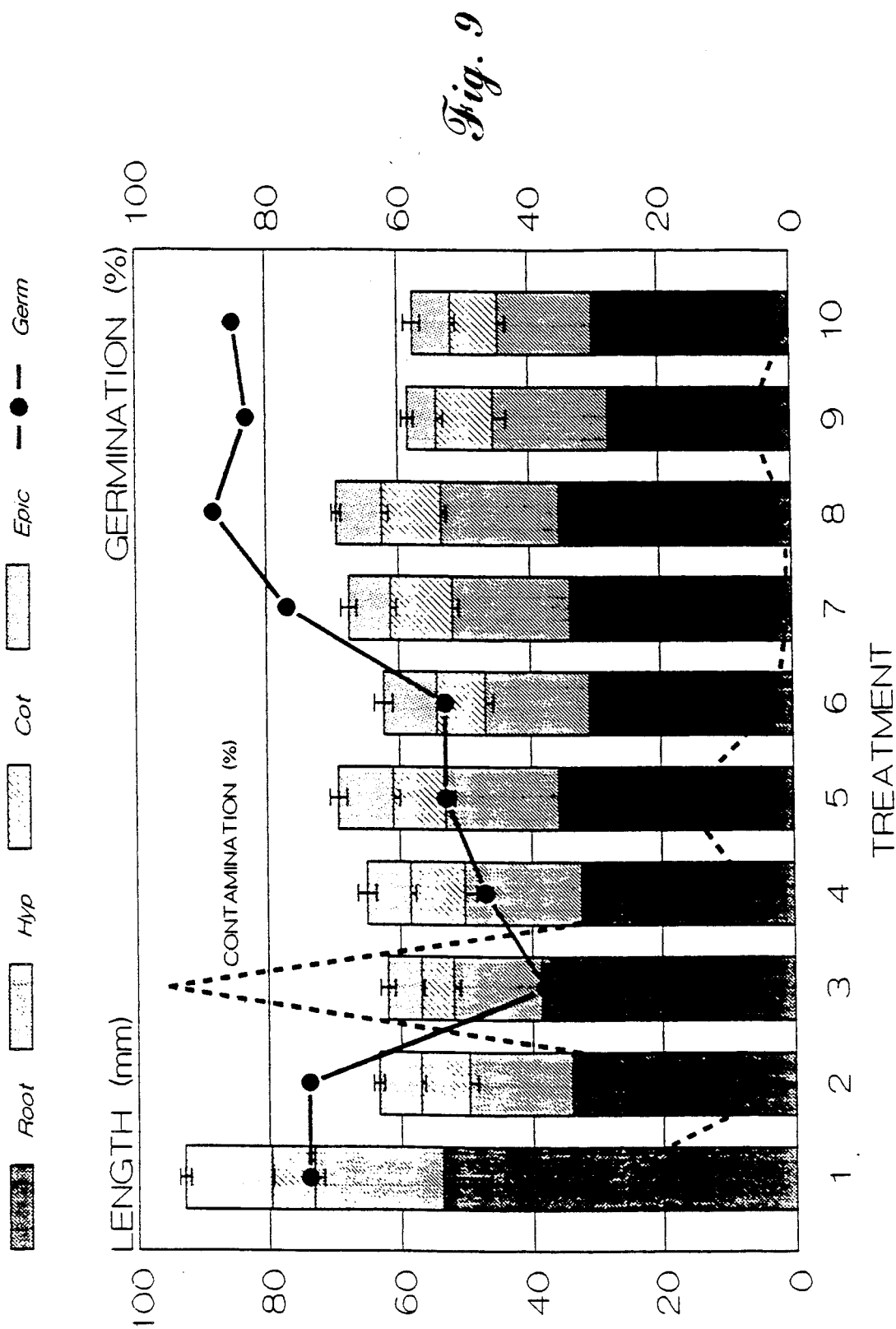
FIG. 9 is a combined histogram and graph showing results of an experiment evaluating the effects of covering plugs containing viable sown embryos with various hydrophobic particulate substances as a way to maintain sterility of the plugs.

Each tray was placed in a standard greenhouse environment after sealing. Germination and growth of the embryos were allowed to proceed for 35 days after sowing. Results with Douglas-fir embryos are shown in FIG. 9 showing data pertaining to a number of parameters. The histogram bars depict length data for roots, hypocotyls, cotyledons, and epicotyls. The solid line connecting the dots shows the percent germination obtained with each treatment. Finally, percent contamination is shown as a dashed line. In determining percent germination, only those embryos that appeared to germinate normally were counted. In determining growth length, only the corresponding portions of normal germinates were considered. Standard error bars are shown with the length data.

The results shown in FIG. 9 indicate that the various surface covering treatments effectively prevent spread of biological contamination. For example, cells receiving treatment "3," where the tops of the vermiculite plugs received no covering, experienced far more biological contamination than other cells that received a top covering. Germinated embryos in cells receiving treatments "7," "8," "9," and "10" developed into plantlets having a height only a few millimeters less than those grown in sterile agar medium in individual petri plates (treatment "1"). In cells lacking a top covering, germination success was halved and height growth of surviving embryos was reduced by about 25%.

With somatic embryos of Norway Spruce, results similar to the Douglas-fir results were obtained. Again, biological contamination experienced with embryos receiving treatment "3" was 97% compared with less than 7% in trays receiving a top covering. Germination was zero in uncovered trays versus 30-70% in trays receiving treatments "7" through "10". A germination yield of 50-80% is a typical range for somatic embryos grown in sterile agar medium according to the prior art.

EXAMPLE 5

In this example, the present method was employed for culturing a representative broadleaf plant. Somatic embryos of "yellow poplar" (*Liriodendron tulipfera* L.) were propagated by conventional techniques on agar medium containing Risser and White's nutrients with 2-percent sucrose. Risser and White, *Physiol. Plant.* 17:620-635 (1964). Forty-eight individual embryos were selected and embedded in individual vermiculite plugs as depicted in the FIG. 6 embodiment. Each plug comprised 1 gram of dry vermiculite to which was added a 3.5-mL volume of nutrient medium. The protective film used to cover each cell was 1.5 mil polypropylene.

After 31 days, the protective film was removed and seedling development assessed by counting the number of true leaves per plant. Of the 48 original embryos sown, the following percentages of the total number of seedlings had 0, 1, 2, or 3 true leaves per seedling:

| # true leaves | % total seedlings |
|---|---|
| 0 | 14.5 |
| 1 | 37.5 |
| 2 | 48.0 |
| 3 | 0 |
| Total: | 100.0 |

Since possession of at least one true leaf is an indication of the plantlet having reached autotrophic status, the above table shows that 85.5 percent of the sown embryos survived to autotrophic status. All these survivors had shown clear signs of continued autotrophic growth after exposure to an intermittently fogged greenhouse environment for 42 days after removal of the film.

Fifty-one embryos were cultivated using the prior-art technique of growth on agar until development of at least one true leaf. After 31 days, only 31% of the control embryos had developed true leaves, each of these having developed three true leaves. Yet, each of these control embryos having true leaves still required transfer and acclimation to a particulate medium. In other words, the present method resulted in a higher percent of autotrophic "survivors" than the control method after the same length of time after sowing of embryos, and also resulted in much more rapid acclimation of the autotrophic seedlings to a soil-like medium than the control method.

EXAMPLE 6

This example provides additional data obtained during an experiment to further evaluate the embodiment discussed above in Example 2. The trays used in these experiments had a height twice the width of each cell. Eighteen trays each having 16 cells were used. The bottom surface of each tray was covered with a plastic film as described in Example 2. A Douglas-fir zygotic embryo was sown in each cell half filled with vermiculite and nutrient medium. In each set of nine trays, the top surface of each of three trays was covered with a film of polypropylene; the top surface of another three trays was covered with a film of polyester and the top surface of the last three trays was covered with a film of polyethylene. Such a scheme yielded three sets of trays each having six trays. Within each set of six trays, three sub-sets of two trays each were subjected to a different lighting regimen that continued until a time after germination when the plantlets had developed sufficiently to allow removal of the top film. The lighting regimens were: (a) 500 $\mu$mol/m$^2$/s from metal halide (MH) and sodium vapor (SV) lamps; (b) 250 $\mu$mol/m$^2$/s from metal halide and sodium vapor lamps; and (c) 250 $\mu$mol/m$^2$/s from mixed fluorescent (F) and incandescent (I) lamps. The light intensity units given are a measure of photon flux density, where the $\mu$mol unit refers to micromoles of photons.

Figure 10:
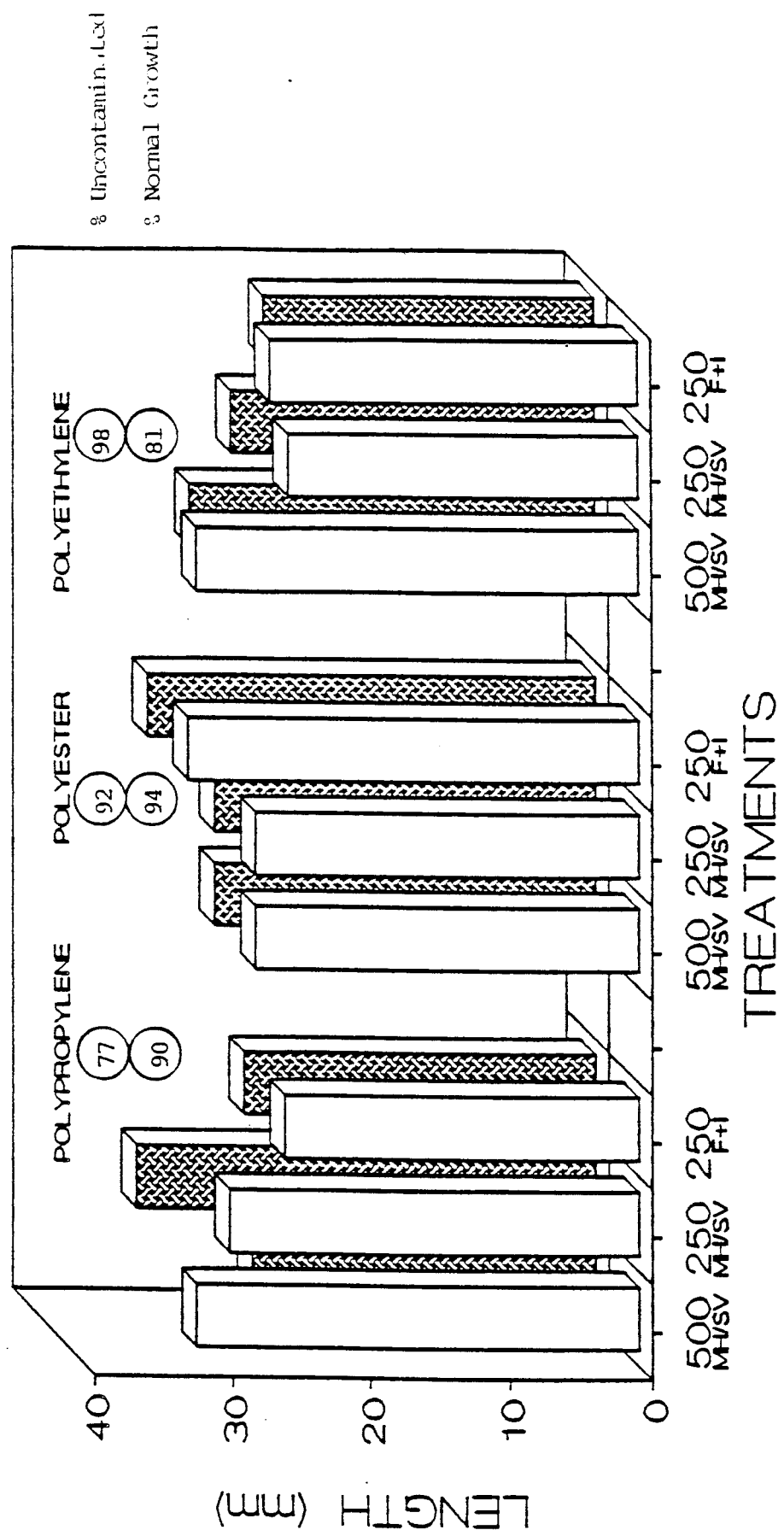
FIG. 10 is a 3-dimensional histogram showing results of an experiment evaluating three types of cover films and three light regimens on embryo germination and growth in deep cells.

FIG. 10 is a three-dimensional histogram showing the results of these experiments, illustrating mean epicotyl lengths measured after the plantlets had been allowed to grow in a greenhouse environment for two months after removal of the top films. For each film type, the circled numbers denote the percentage of clean (uncontaminated with foreign biological growth) cultures and the percentage of clean cultures that germinated normally. From these data, it can be seen that all three films were effective in preventing contamination of the cells by microorganisms and in allowing high levels of normal embryo germination and growth. It appears that all three lighting regimens were effective in their stimulation of early growth of the zygotic embryos.

Having illustrated and described the principles of our invention with reference to several preferred embodiments, it should be apparent to those of ordinary skill in the art that the invention may be modified in arrangement and detail without departing from such principles. For example, instead of gaspermeable covers, the containers may be coupled, as by conduits, to sources of gas needed for plant growth. Also, the covers, such as the cover in FIG. 4, may be opaque with a source of light being provided inside the cover. Also, flexible or nonrigid plug containers can be used, e.g., of treated paper such as ECOPOTS from Lannen Tehtart Oy of Saykla, Finland, if modified, for example, by antimicrobial coatings to resist penetration of microbes and with closed, rather than open, bottoms. Also, suitable plugs include BEAVER BLOCKS, from Beaver Plastics, Ltd. of Edmonton, Alberta, Canada, which can be gas sterilized and top filmed. We claim as our invention all such modifications as come within the true spirit and scope of the following claims.

We claim:

1. A method for mass-producing autotrophic plants from heterotrophic plant material, comprising the steps:
   (a) providing a tray comprising a multiplicity of separate cells adapted for containing plants during development of the plants from a heterotrophic to an autotrophic state, each cell comprised of side walls, an open top, and a top rim, the tray having a top surface defined collectively by the top rims of the cells;
   (b) adding a sufficient amount of particulate growing medium to each of the cells to form a plug in each cell;
   (c) embedding a unit of heterotrophic plant material in each plug;
   (d) adding water, mineral nutrients, and a source of carbon and energy to each plug;
   (e) biologically isolating each cell from all other cells of the tray and protecting the cells from environmental contamination without obstructing passage of sufficient light and gases to the cells necessary for plant growth and development; and
   (f) maintaining the tray in an environment having a temperature and a light level conducive for plant growth and development at least until the units of heterotrophic plant material grow and develop into autotrophic plants.

2. A method for mass-producing autotrophic plants as recited in claim 1 wherein each unit of heterotrophic plant material is a somatic embryo of a plant.

3. A method for mass-producing autotrophic plants as recited in claim 1 wherein each unit of heterotrophic plant material is a zygotic embryo of a plant.

4. A method for mass-producing autotrophic plants as recited in claim 1 including the step of providing the unit of heterotrophic plant material by culturing plant tissue obtained from a plant meristem.

5. A method for mass-producing, from heterotrophic plant material, autotrophic plants capable of being transplanted into soil, the method comprising the steps:
 (a) providing a tray comprising a multiplicity of separate cells adapted for containing plants during development of the plants from a heterotrophic to an autotrophic state, each cell having side walls, an open top, an open bottom, a top rim, and a bottom rim, the tray having a top surface defined collectively by the top rims of the cells and a bottom surface defined collectively by the bottom rims of the cells;
 (b) adding a sufficient amount of particulate growing medium to each of the cells to form a plug in each cell;
 (c) adding water, mineral nutrients, and a source of carbon and energy to each plug;
 (d) ensuring that the tray, plugs, water, mineral nutrients, and source of carbon and energy are sterile;
 (e) embedding a unit of heterotrophic plant material in each plug;
 (f) covering the bottom and top surfaces of the tray so as to maintain each cell in biological isolation from all other cells of the tray and protect the cells from environmental contamination without obstructing passage of light and gases to the cells necessary for plant growth and development;
 (g) maintaining the covered tray in an environment having a temperature and a light level conducive for plant growth and development at least until the units of heterotrophic plant material develop into autographic plants; and
 (h) after the units of heterotrophic plant material develop into autotrophic plants, removing the autotrophic plants from isolation by uncovering at least the top surface of the tray.

6. A method for mass-producing autotrophic plants as recited in claim 5 wherein step (d) comprises sterilizing the tray before forming the plugs in the cells thereof, and wherein the plugs, units of heterotrophic plant material, water, mineral nutrients, and source of carbon and energy are added in a sterile condition to the plugs.

7. A method for mass-producing autotrophic plants as recited in claim 5 including the step, after removing the autotrophic plants from isolation, of watering the plugs to remove at least a portion of the source of carbon and energy from each plug, thereby lessening the capacity of the plugs to support growth of microorganisms.

8. A method for mass-producing autotrophic plants as recited in claim 5 wherein the bottom and top surfaces of the tray are covered by adhering a first plastic film to the bottom surface and adhering a second plastic film to the top surface.

9. A method for mass-producing autotrophic plants as recited in claim 8 wherein the second plastic film is transparent.

10. A method for mass-producing autotrophic plants as recited in claim 8 wherein the second plastic film is adhered to the top surface of the tray using a peelable adhesive and the autotrophic plants are removed from isolation in part by peeling the second plastic film from the top of the tray.

11. A method for mass-producing autotrophic plants as recited in claim 8 wherein the autotrophic plants are removed from isolation in part by puncturing the first plastic film beneath each plug.

12. A method for mass-producing autotrophic plants as recited in claim 11 wherein the first plastic film is adhered to the bottom surface of the tray using a peelable adhesive and the autotrophic plants are removed from isolation in part by peeling the first plastic film from the bottom of the tray.

13. A method for mass-producing autotrophic plants as recited in claim 5 wherein the top surface of the tray is covered by adding to the cells thereof a layer of a particulate hydrophobic material.

14. A method for mass-producing autotrophic plants as recited in claim 13 wherein the bottom surface of the tray is covered by adhering a plastic film thereto.

15. A method for mass-producing autotrophic plants as recited in claim 5 including the step, after step (h), of allowing the autotrophic plants to continue growing in the tray until the plants reach a transplantable size.

16. A method for mass-producing autotrophic plants as recited in claim 5 wherein:
 the plugs of particulate medium are formed in the cells of a first tray; and
 step (f) further comprises providing an empty second tray having a configuration similar to the first tray, wherein the top surface of the first tray is covered by inverting the second tray relative to the first tray and adhering the top surface of the second tray to the top surface of the first tray and the bottom surface of the second tray is covered with a plastic film allowing passage therethrough of light and gases necessary for plant growth and development.

17. A method for mass-producing autotrophic plants as recited in claim 16 wherein the top surface of the second tray is removably adhered to the top surface of the first tray and step (h) comprises detaching the second tray from the first tray.

18. A method for mass-producing autotrophic plants as recited in claim 16 wherein the bottom surface of the second tray is covered with a plastic film by adhering the film to the bottom surface using a peelable adhesive and step (h) comprises peeling the plastic film from the bottom of the second tray.

19. A method for mass-producing, from heterotrophic plant material, autotrophic plants capable of being transplanted into soil, the method comprising the steps:
 (a) providing a tray comprising a multiplicity of separate cells adapted for containing plants during development of the plants from a heterotrophic to an autotrophic state, each cell having side walls, an open top, an open bottom, a top rim, and a bottom rim, the tray having a top surface defined collectively by the top rims of the cells and a bottom surface defined collectively by the bottom rims of the cells;
 (b) adding a sufficient amount of particulate growing medium to each of the cells to form a plug in each cell;
 (c) adding water, mineral nutrients, and a source of carbon and energy to each plug;
 (d) ensuring that the tray, plugs, water, mineral nutrients, and source of carbon and energy are sterile;
 (e) embedding a unit of heterotrophic plant material in each plug;
 (f) peelably adhering a first plastic film to the bottom surface of the tray and a transparent second plastic film to the top surface of the tray so as to maintain each cell in biological isolation from all other cells of the tray and protect the cells from environmental contamination without obstructing passage of light and gases to the cells necessary for plant growth and development;

(g) maintaining the covered tray in an environment having a temperature and a light level conducive for plant growth and development at least until the units of heterotrophic plant material develop into autotrophic plants;

(h) after the units of heterotrophic plant material develop into autotrophic plants, peeling the first and second plastic films from the tray; and (i) watering the plugs to remove at least a portion of the source of carbon and energy from each plug, thereby lessening the capacity of the plugs to support growth of microorganisms.

20. An apparatus for germinating a multiplicity of heterotrophic plant embryos into autotrophic plants capable of being transplanted into soil for continued growth and development, the apparatus comprising:

(a) multiple plugs of particulate material, each plug adapted to serve as a root-growth medium, to physically support a plant embryo during germination and growth of the embryo to an autotrophic plant, and to hold water, mineral nutrients, and a source of carbon and energy for use by the plant embryo during said germination and growth, each plug also having a top surface;

(b) a tray defining a multiplicity of separate, vertically oriented cells, each cell having side walls circumferentially enclosing the cell, an open top, and open bottom, a top rim, and a bottom rim, and the tray having a top surface defined collectively by the top rims of the cells and a bottom surface defined collectively by the bottom rims of the cells, and each cell containing a plug wherein the top surface of the plug is oriented toward the top rim of the respective cell;

(c) a bottom cover attached to the bottom surface of the tray so as to isolate each cell of the tray from incursion of biological contamination from any other cell of the tray and from environmental contamination external to the tray; and (d) a top covering comprising a layer of particulate hydrophobic material placed on the top surface of each plug in the respective cell, the top covering serving to isolate each cell of the tray from incursion of biological contamination from any other cell of the tray and from environmental contamination external to the tray without obstructing passage of gases to each cell of the tray necessary for germination of the embryos.

21. An apparatus as recited in claim 20 wherein the particulate hydrophobic material is selected from a group consisting of glass beads, siliconized glass beads, plastic beads, powdered plastic, and paraffin flakes.

22. An apparatus for germinating a multiplicity of heterotrophic plant embryos into autotrophic plants capable of being transplanted into soil for continued growth and development, the apparatus comprising:

(a) a tray defining a multiplicity of separate, vertically oriented cells each having side walls circumferentially enclosed the respective cell, an open top, an open bottom, a top rim, and a bottom rim, the tray having a top surface defined collectively by the top rim of the cells and a bottom surface defined collectively by the bottom rims of the cells, each cell adapted to contain therein a plug of a particulate medium and dimensioned to contain a plant germinated from an embryo embedded in the plug until the plant has developed sufficiently to survive being exposed to a biologically contaminated environment;

(b) a plug of particulate material provided in each of the cells of the tray, each plug adapted to serve as a root-growth medium, to physically support a plant embryo during germination and growth of the embryo to an autotrophic plant capable of being removed from the cell and transplanted into soil, and to hold water, mineral nutrients, and a source of carbon and energy for use by the plant embryo during said germination and growth;

(c) a top cover removably attached to the top surface of the tray and a bottom cover removably attached to the bottom surface of the tray, wherein said covers when attached to the tray, serve to isolate each cell of the tray from incursion of biological contamination from any other cell of the tray and from environmental contamination external to the tray, and wherein the top cover allows passage therethrough of sufficient light and gases to each cell of the tray necessary for plant growth and development.

23. An apparatus as recited in claim 22 wherein the plug is situated in each cell of the tray so as to leave a head space in the cell for allowing unobstructed emergence of a growing plant from the plug into the cell.

24. An apparatus as recited in claim 23 wherein the plugs in the cells have a height dimension and the head space in each cell has a height at least equal to the height of the plug.

25. An apparatus as recited in claim 22 wherein the bottom cover is puncturable.

26. An apparatus as recited in claim 22 wherein the bottom cover is permeable to gases necessary for plant growth and development.

27. An apparatus as recited in claim 22 wherein the bottom cover is removably attached to the bottom surface of the tray by a peelable contact adhesive.

28. An apparatus as recited in claim 22 wherein the top cover is a transparent plastic film.

29. An apparatus as recited in claim 22 wherein the top cover has a permeability to water vapor within a range of about zero to about 1300 GTR units.

30. An apparatus as recited in claim 9 wherein the top cover has a permeability to water vapor within a range of about zero to about 6 VTR units.

31. An apparatus as recited in claim 22 wherein the top cover is removably attached to the top surface of the tray by a peelable contact adhesive.

32. An apparatus as recited in claim 22 wherein the walls of the tray are transparent.

33. An apparatus as recited in claim 22 comprising first and second trays each with a bottom cover attached to the bottom surface of the respective tray, wherein the top cover of the first tray comprises the second tray attached in an inverted orientation to the first tray such that the top surface of the first tray is affixed to the inverted top surface of the second tray.

34. An apparatus as recited in claim 33 wherein the bottom cover of the second tray is transparent.

35. An apparatus as recited in claim 33 wherein the inverted top surface of the second tray is removably affixed to the top surface of the first tray by a peelable contact adhesive.

36. An apparatus as recited in claim 33 wherein the bottom cover of the second tray is removably attached to the inverted bottom surface of the second tray by a peelable contact adhesive.

37. An apparatus for germinating a multiplicity of heterotrophic plant embryos into autotrophic plants capable of being transplanted into soil for continued growth and development, the apparatus comprising:
(a) multiple plugs of particulate material, each plug adapted to serve as a root-growth medium, to physically support a plant embryo during germination and growth of the embryo to an autotrophic plant, and to hold water, mineral nutrients, and a source of carbon and energy for use by the plant embryo during said germination and growth, each plug also having a top surface;
(b) a tray defining a multiplicity of separate, vertically oriented cells, each cell having side walls circumferentially enclosing the cell, an open top, an open bottom, a top rim, and a bottom rim, and the tray having a top surface defined collectively by the top rims of the cells and a bottom surface defined collectively by the bottom rims of the cells, and each cell containing a plug wherein the top surface of the plug is oriented toward the top rim of the respective cell;
(c) a bottom cover attached to the bottom surface of the tray so as to isolate each cell of the tray from incursion of biological contamination external to the tray; and
(d) a top covering comprising a layer of particulate hydrophobic material placed on the top surface of each plug in the respective cell, the top covering serving to isolate each cell of the tray from incursion of biological contamination from any other cell of the tray and from environmental contamination external to the tray without obstructing passage of gases to each cell of the tray necessary for germination of the embryos, wherein the particulate hydrophobic material is selected from a group consisting of glass beads, siliconized glass beads, plastic beads, powdered plastic, and paraffin flakes, and wherein the particulate hydrophobic material is coated with an antimicrobiological agent.

38. An apparatus for germinating a multiplicity of heterotrophic plant embryos into autotrophic plants capable of being transplanted into soil for continued growth and development, the apparatus comprising:
(a) a tray defining a multiplicity of separate, vertically oriented cells each having side walls circumferentially enclosing the respective cell, an open top, an open bottom, a top rim, and a bottom rim, and the tray having a top surface defined collectively by the top rims of the cells and a bottom surface defined collectively by the bottom rims of the cells, each cell adapted to contain therein a plug of a particulate material and dimensioned to contain a plant germinated from an embryo embedded in the plug until the plant has developed sufficiently to survive being exposed to a biologically contaminated environment;
(b) a plug of particulate material provided in each cell of the tray, each plug adapted to serve as a root-growth medium and to physically support a plant embryo during germination and growth of the embryo to an autotrophic plant capable of being removed from the cell and transplanted into soil, each plug adapted to hold water, mineral nutrients, and a source of carbon and energy for use by the plant embryo, and each plug situated in the respective cell of the tray so as to leave a head space in the cell for allowing unobstructed emergence of a growing plant from the plug into the cell;
(c) a first plastic film attached to the bottom surface of the tray so as to isolate each cell of the tray from incursion of biological contamination from any other cell of the tray and from environmental contamination external to the tray, the first plastic film permeable to gases necessary for plant growth and development; and
(d) a second plastic film removably adhered to the top surface of the tray so as to isolate each cell of the tray from incursion of biological contamination from any other cell of the tray and from environmental contamination external to the tray without obstructing passage of sufficient light and gases to each cell of the tray necessary for plant growth and development.

* * * * *

UNITED STATES PATENT AND TRADEMARK OFFICE
CERTIFICATE OF CORRECTION

PATENT NO. : 5,119,588
DATED : June 9, 1992
INVENTOR(S) : Robert Timmis, et al

It is certified that error appears in the above-indentified patent and that said Letters Patent is hereby corrected as shown below:

On the title page, item [56] References Cited, U.S. PATENT DOCUMENTS, the following missing documents should be added to the list:
  U.S. Patent No. 4,672,035 of Davidonis, et al.
  U.S. Patent No. 4,777,762 of Redenbaugh et al.
  U.S. Patent No. 3,971,160 of Vajtay.

[54] Abstract, line 6, "embeddeed" should be --embedded--.
Column 2, line 23, "embryos Hence" should be --embryos. Hence--.
Column 3, line 4, "encourage" should be --encourages--.
Column 26, claim 29, line 44, "water vapor" should be --oxygen gas--.

Signed and Sealed this

Twentieth Day of September, 1994

Attest:

BRUCE LEHMAN

Attesting Officer

Commissioner of Patents and Trademarks